United States Patent [19]
Brooker

[11] Patent Number: 5,491,343
[45] Date of Patent: Feb. 13, 1996

[54] HIGH-SPEED MULTIPLE WAVELENGTH ILLUMINATION SOURCE, APPARATUS CONTAINING THE SAME, AND APPLICATIONS THEREOF TO METHODS OF IRRADIATING LUMINESCENT SAMPLES AND OF QUANTITATIVE LUMINESCENCE RATIO MICROSCOPY

[76] Inventor: Gary Brooker, 9212 Bentridge Ave., Potomac, Md. 20854

[21] Appl. No.: 217,883
[22] Filed: Mar. 25, 1994
[51] Int. Cl.⁶ .................................................. G01N 21/64
[52] U.S. Cl. ...................................... 250/458.1; 250/459.1
[58] Field of Search ................................ 250/459.1, 458.1

[56] References Cited

U.S. PATENT DOCUMENTS

| | | | |
|---|---|---|---|
| 5,053,626 | 10/1991 | Tillotson | 250/458.1 |
| 5,102,625 | 4/1992 | Milo | 422/82.07 |
| 5,294,799 | 3/1994 | Aslund et al. | 250/458.1 |
| 5,332,905 | 7/1994 | Brooker et al. | 250/458.1 |

FOREIGN PATENT DOCUMENTS

| | | | |
|---|---|---|---|
| 298309 | 2/1992 | Germany | 250/458.1 |

OTHER PUBLICATIONS

R. L. McKenzie and K. P. Gross, "Two–photon excitation of nitric oxide fluorescence as a temperature indicator in unsteady gasdynmaic processes." *Applied Optics*, vol. 20, No. 12 (Jun. 15, 1981) pp. 2153–2165.
International Search Report (International application No. PCT/US95/02682).

*Primary Examiner*—Constantine Hannaher
*Attorney, Agent, or Firm*—Oblon, Spivak, McClelland, Maier & Neustadt

[57] ABSTRACT

A high-speed, non-mechanical multiple wavelength illumination source is provided, which contains a first light source, a second light source providing a different wavelength of light, and a controlling means for controlling electric current to the first and second light sources. The illumination source is particularly useful in an improved apparatus for quantitative luminescence ratio photometry and/or luminescence ratio imaging. Methods of luminescence emission ratio photometry and luminescence emission ratio imaging using the illumination source and apparatus are also provided. The present invention offers particular advantages in photomicroscopy and in microscopic imaging.

21 Claims, 5 Drawing Sheets

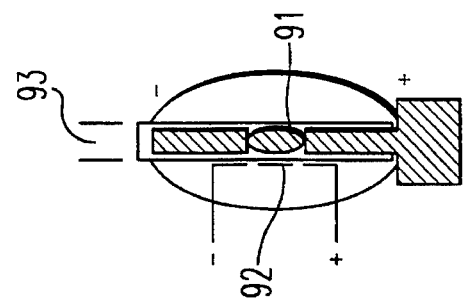
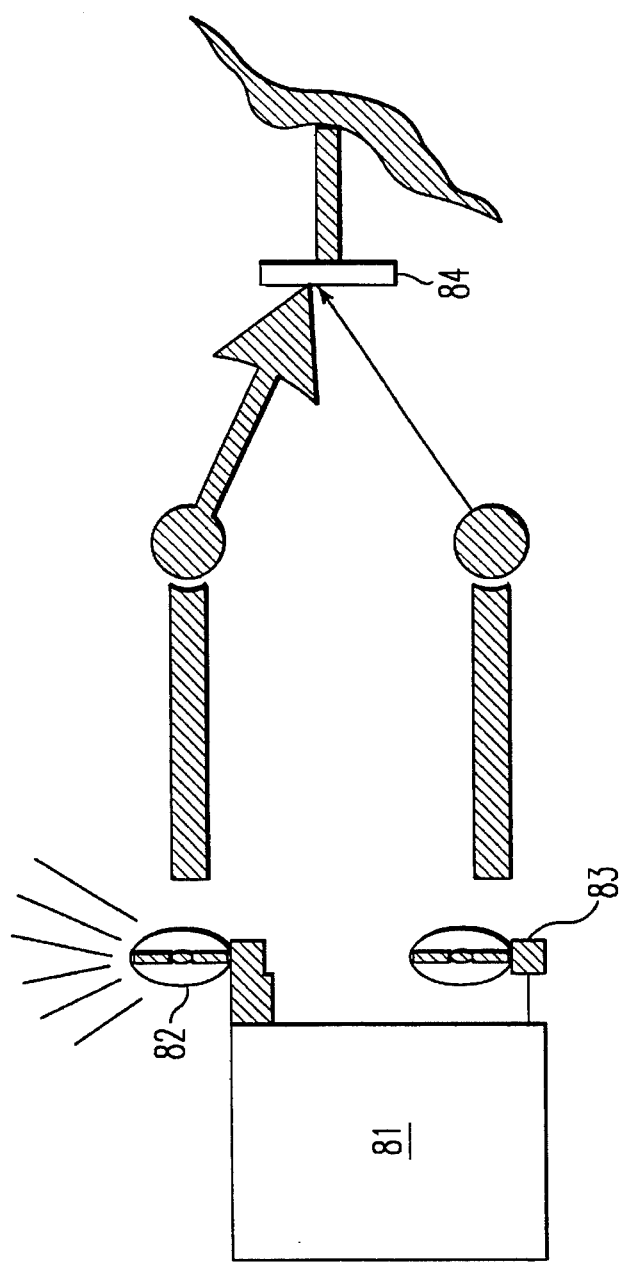
FIG. 9
FIG. 8

HIGH-SPEED MULTIPLE WAVELENGTH ILLUMINATION SOURCE, APPARATUS CONTAINING THE SAME, AND APPLICATIONS THEREOF TO METHODS OF IRRADIATING LUMINESCENT SAMPLES AND OF QUANTITATIVE LUMINESCENCE RATIO MICROSCOPY

BACKGROUND OF THE INVENTION

1. Field of the Invention

The present invention concerns a high-speed multiple wavelength illumination source, an apparatus containing the illumination source, and methods of irradiating luminescent samples and of quantitative ratio luminescence microscopy using the illumination source and apparatus.

2. Discussion of the Background

A growing field in quantitative fluorescence microscopy is ratio imaging, which involves sequentially illuminating the same field of a specimen with two or more wavelengths of light, capturing each image, and then dividing the intensities of the two resultant images (or areas of interest within the images) to obtain an intensity ratio of the two images. In the typical case, the specimen is labeled with a fluorescent dye, the fluorescence ratio of which is related to a quantitative property of the dye or to an interaction with another substance which affects the fluorescence of the fluorescent dye. One example of a method and apparatus for multiple emission ratio photometry and multiple emission ratio imaging are described in U.S. application Ser. No. 07/935,873, filed on Aug. 26, 1992, now U.S. Pat. No. 5,332,905, the entire contents of which are incorporated herein by reference.

In quantitative fluorescence ratio imaging or fluorescence ratio photometry (also known as "quantitative ratio imaging" or "quantitative ratio photometry"), a specimen containing a fluorescent compound or species is illuminated with two different wavelengths of light ($\lambda_1$ and $\lambda_2$). The respective resultant fluorescent intensities ($I_1$ and $I_2$) are measured in one or more pre-determined areas of interest on the fluorescent specimen with a photometer. Alternatively, the fluorescent intensities $I_1$ and $I_2$ can be measured as an array of pixels by an imaging detector, so that an image of the fluorescent specimen can be produced and/or observed.

The relationship between the ratio of the fluorescent emission intensities ($I_1/I_2$) at each of the two respective excitation wavelengths $\lambda_1$ and $\lambda_2$ is a function of the concentration of the substances which associate or interact with the fluorescent dye. The concentration of the fluorescence-affecting substance ([Substance]) is defined by the following Equation (1):

$$[\text{Substance}] = f \cdot \frac{[I_1 @ \lambda_1][\text{Dye}]}{[I_2 @ \lambda_2][\text{Dye}]} \quad (1)$$

The intensities may be measured at the same location(s) of the sample. Accordingly, the concentration of fluorescent compound ([Dye]) is the same at both excitation wavelengths. Thus, the only difference in measurements according to Equation (1) is the wavelength of excitation. Therefore, the dye concentration term cancels out from Equation (1), and the equation reduces to:

$$[\text{Substance}] = f \cdot \frac{[I_1 @ \lambda_1]}{[I_2 @ \lambda_2]} \quad (2)$$

In current practice, the rate at which the ratio image of the sample can be obtained is limited by the frequency at which the specimen can be alternately illumined with each of the excitation wavelengths. The change in wavelength is in all cases controlled by some mechanical device (such as a filter wheel) to alternate the wavelength of illumination. The most typical method of alternating the wave-length of excitation is to illuminate the sample with an arc lamp 11 (which provides a broad spectrum of light) and to change the wavelength of illumination by switching filters on a filter wheel 12 which only pass the desired wavelength of light to the specimen 13, as shown in FIG. 1.

Another method is to alternate between two sources monochromatic light focused upon the specimen. This is presently accomplished by a mechanical means 21 located between the two light sources 22 and 23 and the specimen 24, as shown in FIG. 2. Mechanical means 21 typically blocks one beam of light selectively, by either the alternate opening and closing of shutters or the rotation of a chopper wheel. After passing through mechanical means 21, the light beam passes the filter 25 or 26 before irradiating specimen 24.

The approaches employing a filter wheel, shutters or a chopper blade are limited by the speed of the mechanical movements required to change filters, shutters or chopper blades. By contrast, the speed with which a detector can be altered to make or to process a new measurement is limited only by the electronic circuitry controlling the measuring apparatus. In general, electronic impulses can be changed at a much faster rate than a mechanical device, such as a filter wheel, shutters or a chopper blade. Accordingly, it is a desirable goal in the photometric arts to provide a means for (repeatedly) changing or switching between light sources of different wavelengths at the speed of electronic circuitry, rather than at the speed of mechanical motions.

In addition, mechanically switching filters, shutters or chopper blades also causes vibrations in the measuring apparatus. Such vibrations can lead to changes in the location of the sample being measured (especially when a specimen is being viewed under a microscope), thus destroying the reliability of the data obtained from the measurements.

The fastest filter wheel presently available provides the capability to switch between different excitation wavelengths in a period of time of from about 2.5–5 milliseconds (ms). However, such a filter wheel is in constant motion during operation. The constant motion limits the duration with which the sample can be irradiated, and also introduces non-uniform interference patterns in filtering the excitation light.

SUMMARY OF THE INVENTION

Accordingly, one object of the present invention is to provide a novel illumination source having an electronic means for changing between two wavelengths of light.

A further object of the present invention is to provide a novel apparatus for irradiating a luminescent sample, comprising the illumination source.

A further object of the present invention is to provide novel methods of luminescent emission ratio photometry and multiple emission ratio imaging using the illumination source and apparatus.

A further object of the present invention is to provide novel methods and apparatuses for conducting emission ratio imaging and emission ratio photometry which avoid introducing the risks of vibration inherent in filter wheels, filter arms, chopper wheels, and other previous devices for changing the wavelength of irradiation or of excitation light.

Another object of the present invention is to provide novel methods and apparatuses for irradiating a sample which enables switching between different wavelengths and/or intensities of light at a rate which is not limited by mechanical switching devices.

A further object of the present invention is to provide novel methods and apparatuses for conducting luminescent emission ratio photometry and imaging, capable of monitoring changes in the interaction between (kinetic phenomena involving) a luminescent substance and a luminescence-affecting substance on a millisecond- and submillisecond scale.

A further object of the present invention is to provide novel methods and apparatuses for conducting fluorescent emission ratio photometry and imaging, capable of monitoring kinetic phenomena involving a fluorescent substance and a fluorescence-affecting substance on a millisecond- and submillisecond scale.

Various other objects, features and attendant advantages of the present invention will be more fully appreciated as the same becomes better understood from the following detailed description when considered in connection with the accompanying drawings in which like reference characters designate like or corresponding parts throughout the several views and wherein the following detailed description of the preferred embodiments have been provided by the present invention, which overcomes the problems described above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8 illustrates an alternative embodiment of the present illumination source, in combination with a beam combiner; and FIG. 9 illustrates an alternative embodiment of the present illumination source comprising a multiple arc lamp employing a pilot arc and a running arc.

DESCRIPTION OF THE PREFERRED EMBODIMENTS

Figure 1:
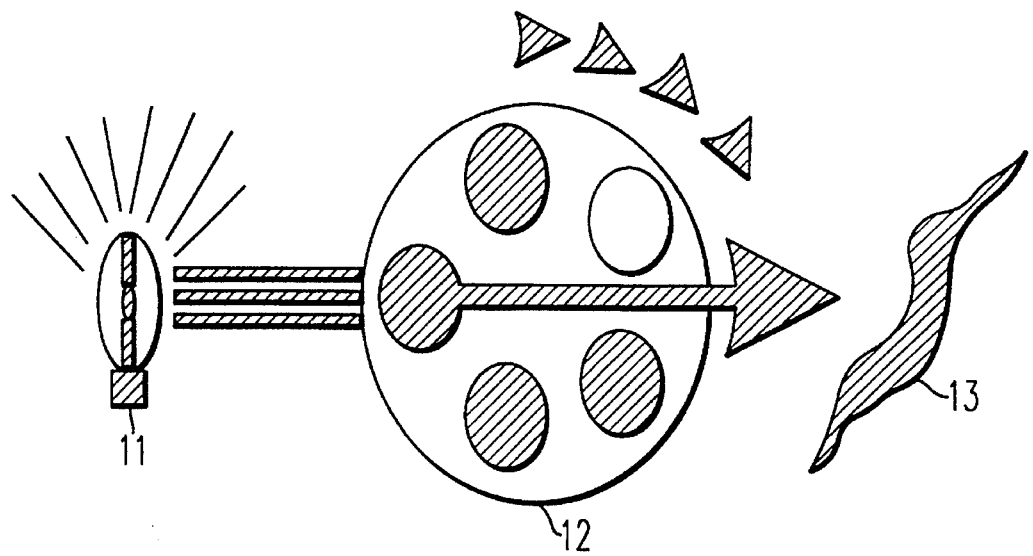
FIG. 1 illustrates a conventional method of changing the wavelength of irradiation by use of a filter wheel.
Figure 2:
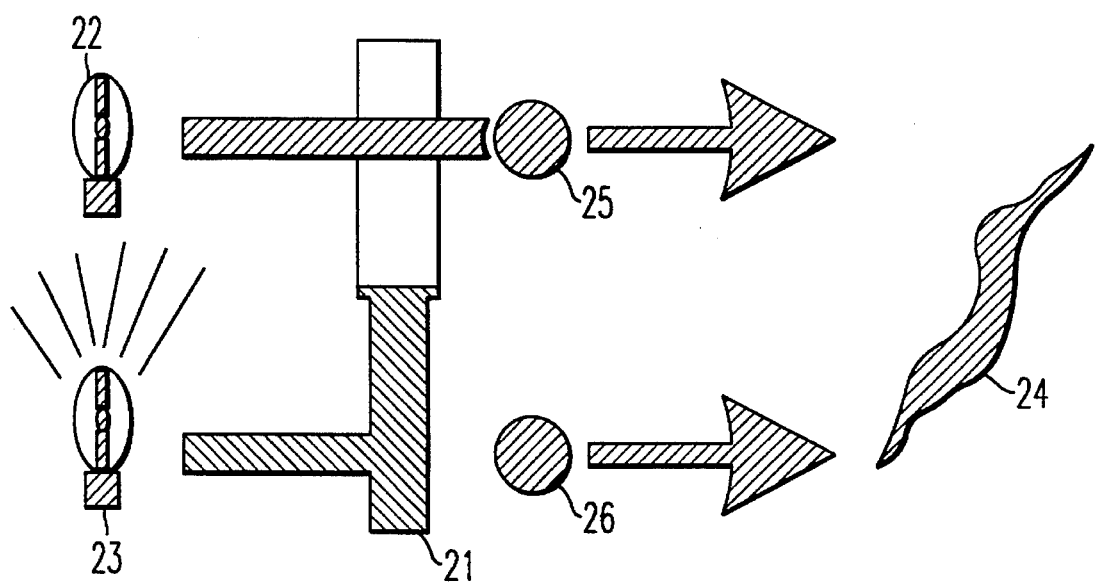
FIG. 2 illustrates a conventional method of changing the wavelength of irradiation using shutters or a rotating chopper wheel.
Figure 3:
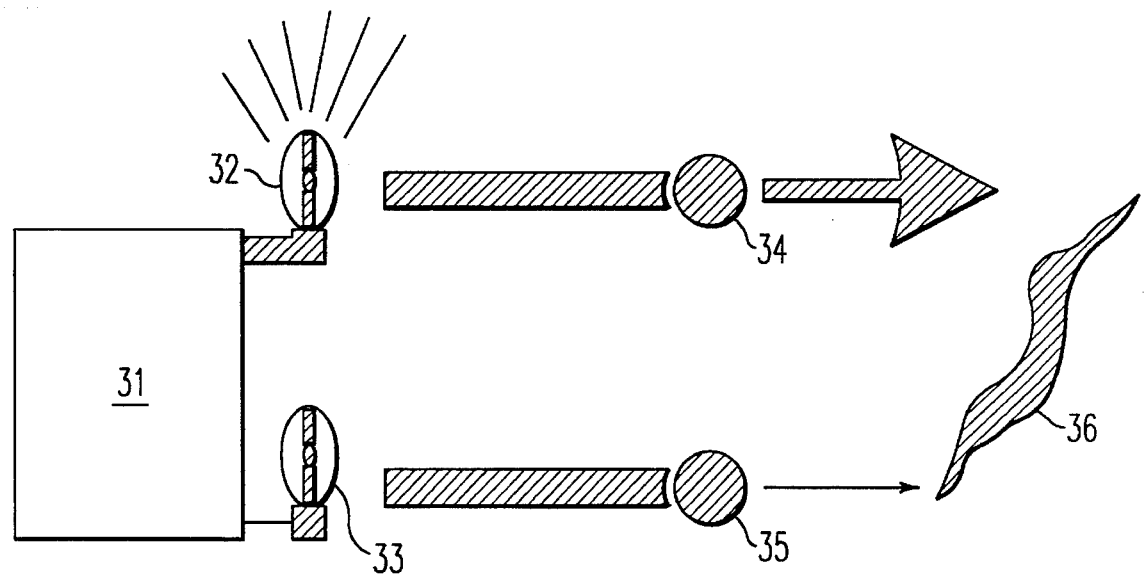
FIG. 3 illustrates a method of changing the wavelength of excitation energy by electronically controlling two independent light sources.

Referring now to the drawings, wherein like reference numerals designate identical or corresponding parts throughout the several views, and more particularly to FIG. 3 thereof, a first step of the present method of sequentially irradiating a sample with two different wavelengths of light and an apparatus suitable for the method are statically illustrated. In FIG. 3, electronic current control means 31 provides a relatively high current to first light source 32. The first light source 32 generates excitation light of a first wavelength $\lambda_1$, which passes through a first wavelength-specific filter 34, then strikes (or irradiates) a specimen 36 containing a luminescent (preferably fluorescent) substance. At the same time, a relatively low current is provided by electronic current control means 31 to a second light source 33. The relative proportion of current to second light source 33 is sufficiently low as to not interfere with or affect the luminescent emission(s) of the specimen 36 caused by irradiation with the excitation light of first wavelength $\lambda_1$, generated by first light source 32.

As is understood in the art, the energy of light is inversely proportional to its wavelength. The terms "energy" and "wavelength" can be used interchangeably with regard to light. Further, the terms "luminescent" and "luminescence" refer to both fluorescent and phosphorescent phenomena.

To change the wavelength of excitation light, electronic current control means 31 alternately changes the relative amounts of electric current flowing through each light source (e.g., arc lamps 32 and 33). As a result, electronic current control means 31 also alternately changes the intensity of first and second light sources 32 and 33. From the first step shown in FIG. 3, increasing the current flowing through second light source 33 and decreasing the current flowing through first light source 32 changes the wavelength of light striking sample 36.

Changing the current in this manner causes an instantaneous change in the light intensity of each light source. In the case of a two-source system, if the current is increased in the first lamp 32 (which controls $\lambda_1$) and the current is decreased in the second lamp 33 (which controls $\lambda_2$), the resultant effect is to illuminate the specimen 36 with $\lambda_1$ light. If the current is then increased in the second lamp 33 (which controls $\lambda_2$) and the current is decreased in the first lamp 32 (which controls $\lambda_1$), the resultant effect is to illuminate the specimen 36 with $\lambda_2$ light. The cycle can then be repeated at any frequency of which electronic current control means 31 is capable of providing, to alternately illuminate the specimen at these two wavelengths of light.

One may also change and/or alternately switch between different intensities of the light generated by first and second light sources in the same manner described above for changing or alternately switching between different wavelengths of light. Thus, when changing and/or alternately switching between different intensities of light, the first and second light beams provided by the first and second light sources and any wavelength-selecting means associated therewith may be the same ($\lambda_1=\lambda_2$) or different ($\lambda_1 \neq \lambda_2$).

Thus, one aspect of the present invention concerns a method of irradiating a sample, comprising the steps of:

(A) irradiating said sample with light having a first wavelength, a first intensity or both a first wavelength and a first intensity; and, (B) irradiating said sample with light having a second wavelength, a second intensity or both a second wavelength and a second intensity within a period of time of from 1 nanosecond (1 ns) to 1 second (1 s) of said irradiating step (A).

For convenience, the following discussion(s) will focus on methods and apparatuses for changing or alternately switching between different wavelengths of light, although the same techniques may be applied to changing or alternately switching between different intensities of light.

Irradiating step (A) of the present method of irradiating a sample preferably comprises passing an electric current having a first value through a first light source, and irradiating step (B) preferably comprises passing an electric current having a second value through a second light source. More preferably, irradiating step (A) further comprises passing an electric current having a third value through the second light source, wherein the third value is less than the second value of the electric current, and irradiating step (B) further comprises passing an electric current having a fourth value through the first light source, wherein the fourth value is less than the first value of the electric current.

In a further aspect of the present invention, the method of irradiating a sample further comprises, after irradiating step (A) and before irradiating step (B), the steps of:

(A') decreasing the first value of the electric current in the first light source to the fourth value of the electric current, and (A") increasing the third value of the electric current in the second light source to the second value of the electric current.

In a further aspect of the present invention, the rapid and precise repeatability of the method of irradiating a sample is advantageously used. Thus, the method further comprises, within a period of time of from 1 ns to 1 s after irradiating step (B), repeating irradiating step (A).

A further aspect of the present invention concerns apparatus for sequentially irradiating a sample with two or more wavelengths, intensities, or wavelengths and intensities of light, comprising:

(A) a first light source which generates a first light beam having a first wavelength, a first intensity or both a first wavelength and a first intensity;

(B) a second light source which generates a secod light beam having a second wavelength, a second intensity or both a second wavelength and a second intensity, wherein said second wavelength differs from said first wavelength, said second intensity differs from said first intensity, or said second wavelength and said second intensity differ from said first wavelength and said first intensity; and (C) a controlling means for controlling electric current to each of said first and second light sources, said controlling means being electrically connected to each of said first and second light sources.

Each of the first and second wavelengths of light may represent the mean or average wavelength of a band or range of wavelengths of light (for example, from 300 to 340 nm or from 380 to 400 nm), or may represent a band or range greater than a selected or desired wavelength [e.g., a "long pass" filter, such as one which allows light having a wavelength of 500 nm or greater to pass). Thus, the present apparatus may further comprise first and second means for selecting a band of light, in which the means may be a filter, a grating monochromator or any other equivalent device providing a selected band of wavelengths of light. The present means for selecting a band of light intercepts each light beam after being generated by a light source and prior to striking or irradiating the sample.

Although a band of light having any desired band width may be selected, preferably, each of the first and second bands of wavelengths have a band width of 40 nm or less, or are greater than or equal to a desired or selected wavelength. Such bands of wavelengths of light may be provided by a first filter and a second filter, respectively placed in the paths of the light generated by the first and second light sources. Such filters may be made of one or more suitable, conventional wavelength-selective materials, and are generally known in the art. Alternatively, a conventional grating monochromator which provides the desired excitation wavelength may be substituted for either or both of the first and second filters. Thus, in an advantageous embodiment, the present apparatus sequentially irradiates a sample with two or more wavelengths of light. The first wavelength is a mean or average wavelength of a first band of wavelengths, the second wavelength is a mean or average wavelength of a second band of wavelengths, and each of the first and second bands of wavelengths either (a) have a band width of 40 nm or less, or (b) are greater than or equal to a desired or pre-selected wavelength.

In a further aspect of the present invention, the first light source (A) in the apparatus for sequentially irradiating a sample with two or more wavelengths of light is a first arc, and the second light source (B) is a second arc. In one embodiment of the apparatus, the first arc is a first arc lamp, and the second arc is a second arc lamp.

In the present invention, any arc lamp which provides sufficient excitation light to produce one or more luminescent emissions in the sample may be used. Any light source may be, for example, an arc lamp having a wattage of from 10 to 2000 W. The choice of a suitable arc lamp may be determined based on the amount of illumination (excitation light) needed, on the intensity of light produced by the light source, and/or on any other pertinent factor(s). One advantage of the present method and apparatus lies in the flexibility of light sources which may be employed. For example, the first source may be an arc lamp which provides a first intensity of light (e.g., a 500 watt (W) arc lamp), and a second light source may provide a second, relatively higher or lower intensity of light (e.g., a 10 W or 2000 W arc lamp).

A further advantage of the present method and apparatus is that the sample can be irradiated with two different wavelengths of light simultaneously. For example, a first light source may provide a first wavelength of irradiation light which excites the luminescent compound or dye, and the second light source may provide a second wavelength of irradiation light to "uncage" or activate a photoactivatable, caged probe in a manner known in the art (see J. A. McCray et al, Ann. Rev. Biophys. Chem., vol. 18, page 239 (1989), and Item No. 4287 of the catalog distributed by Molecular Probes, Junction City, Oreg.). Alternatively, the first light source may provide continuous irradiation of the sample with a first wavelength of light, and the second light source may provide intermittent irradiation of the sample (e.g., "flash" irradiation). Accordingly, the present method is not limited to any particular temporal sequence of irradiating steps.

The present invention may also be expanded to encompass more than two light sources and more than two wavelengths of light. Theoretically, there is no limit to the number of light sources which can be used, as long as the light beams generated can be directed to the sample for irradiation. Similarly, there is no limit to the number of wavelengths of light which can be selected, as long as each of the selected wavelengths can be produced and used to irradiate the sample.

Figure 4:
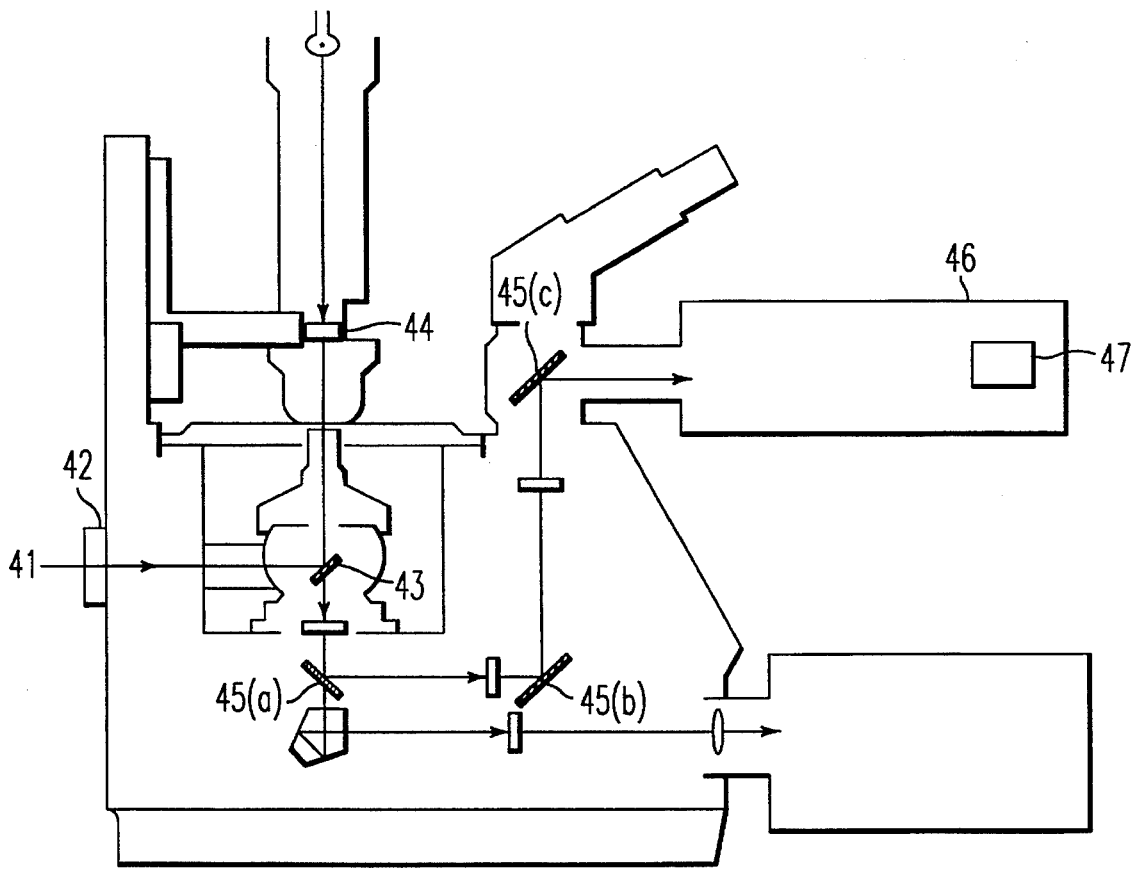
FIG. 4 is a schematic diagram of an apparatus for conducting emission ratio photometry and/or emission ratio imaging.

FIG. 4 shows an exemplary diagram of a particular apparatus for conducting emission ratio photometry or imaging. The light source 41 provides light of a suitable excitation energy to result in the desired emission phenomena. In the present invention, light source 41 is preferably the apparatus shown in FIG. 3, comprising electronic current control means 31 and first and second light sources 32 and 33. The light from light source 41 passes through filtering apparatus 42 (which may comprise, as shown in FIG. 3, first and second filters 34 and 35), and is then reflected by dichroic mirror 43 towards the sample mounting area or platform 44. The excitation light is then absorbed by the sample, placed or mounted on mounting platform 44. The sample contains a luminescent (fluorescent or phosphorescent) substance or a luminescent complex, the complex comprising a luminescent substance and a luminescence-affecting species. The luminescent substance or complex becomes excited, then emits light of a lower energy and longer wavelength than the excitation light. The light emitted from the luminescent substance passes through dichroic mirror 43, and is reflected by a series of mirrors 45(a), 45(b) and 45(c) to detector 46, where the emission is measured.

The process is then repeated to obtain a second emission. For a sample having one or more additional luminescent substances or complexes, the process is repeated twice more for each additional luminescent substance or complex. Each of the emissions is monitored independently by a suitably-equipped detector.

According to the present invention, one or more lamp sources are positioned in a manner enabling one to illuminate the specimen as in the conventional method(s) described above using shutters or a chopper, except that such mechanical devices for changing the light wavelength are not used for the practice of the present invention.

Figure 5:
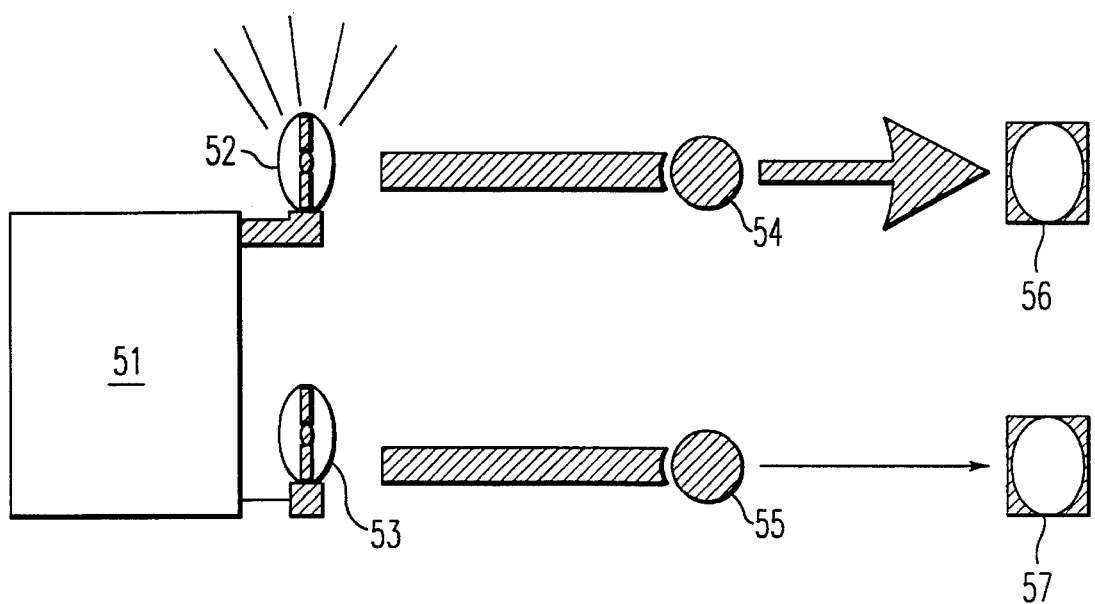
FIG. 5 illustrates the performance characteristics of a multi-arc switching source.

As illustrated in FIG. 5, changing from a first wavelength of excitation light ($\lambda_1$) to a second wavelength of excitation light ($\lambda_2$) is accomplished electronically using electronic current control means 51. Preferably, the controlling means for controlling the electric current to the light sources is provided by solid-state electronic circuitry.

In the static illustration provided by FIG. 5, electronic current control means 51 provides a relatively high current to first light source 52, the active light source in this static illustration. For example, the relative percentage of current which goes to the first light source may be >90% of the total current supplied by electronic current control means 51 to both first light source 52 and second light source 53. In view of a preference toward maintaining a small current through the inactive light source, it is preferable for the maximum relative percentage of current to the active light source to be from 95 to 99% of the total current supplied by electronic current control means to all light sources. Thus, in the static illustration of FIG. 5, the relative percentage of current supplied to the first light source 52 is preferably 95–99%, and the relative percentage of current supplied to the second light source 53 is preferably 1–5%, of the total current supplied by electronic current control means 51 to both first light source 52 and second light source 53.

The first light source 52 provides a first light beam, which passes through a first wavelength-specific filter 54, generating light of a first wavelength $\lambda_1$, which then strikes a first detector 56. At the same time, a relatively low current is provided by electronic current control means 51 to a second light source 53, which provides a second light beam which passes through a second wavelength-specific filter 55, generating light of a second wavelength $\lambda_2$, which then strikes a second detector 57.

To switch between different wavelengths of excitation light, electronic current control means 51 alternately changes the amount of electric current flowing through each light source 52 and 53, thus alternately changing the relative intensity of each light source 52 and 53. Light sources 52 and 53 are, for example, arc lamps. By increasing the current flowing through light source 53 and decreasing the current flowing through first light source 52, the intensities of each wavelength of light striking first and second detectors 56 and 57 change relative to each other. Alternatively or additionally, one may switch between different intensities of excitation light by using electronic current control means 51 to alternately change the relative amount of electric current flowing through each light source 52 and 53.

When the intensity of a light source (e.g., an arc lamp) is in a reduced state, it is advantageous to maintain a minimum current in the light source. A "minimum current" in a light source, and more specifically, in an arc lamp, is one sufficient to support a small arc, but one which does not cause interference with measurement of the emission resulting from irradiation with light from the light source having a relatively large current passed through it. One might think of the arc operating at minimum current as being in a "pilot" state. Currents as low as 1% or lower of the maximum current applied to the lamp can keep the arc active. As long as the arc is active, then application of increased current instantaneously leads to a new level of illumination. If the arc in the pilot state extinguishes, then rapid switching may not be possible. A relatively long amount of time (e.g., on the order of 1–20 seconds) is necessary to re-establish the arc.

Keeping the arc in a pilot state also makes it easy to instantly establish a new and stable light intensity. The stability and reproducibility of the new intensity may be advantageously enhanced by calibration with appropriate standards, prior to irradiating or measuring emission intensities of a sample containing an unknown concentration distribution of luminescent species or luminescence-affecting species. Thus, arc lamp sources can be advantageously used to provide a wide dynamic range of rapidly switched light intensities, with the important feature of instantaneous non-mechanical vibration-free electronic control.

Figure 6A:
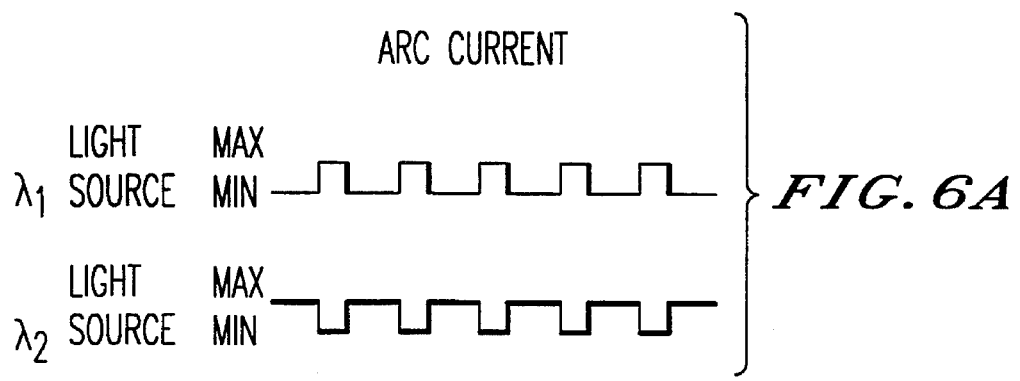
FIGS. 6A and 6B depict graphically the changes in arc current and light output for each of two independent light sources as a result of electronic control and switching.
Figure 6B:
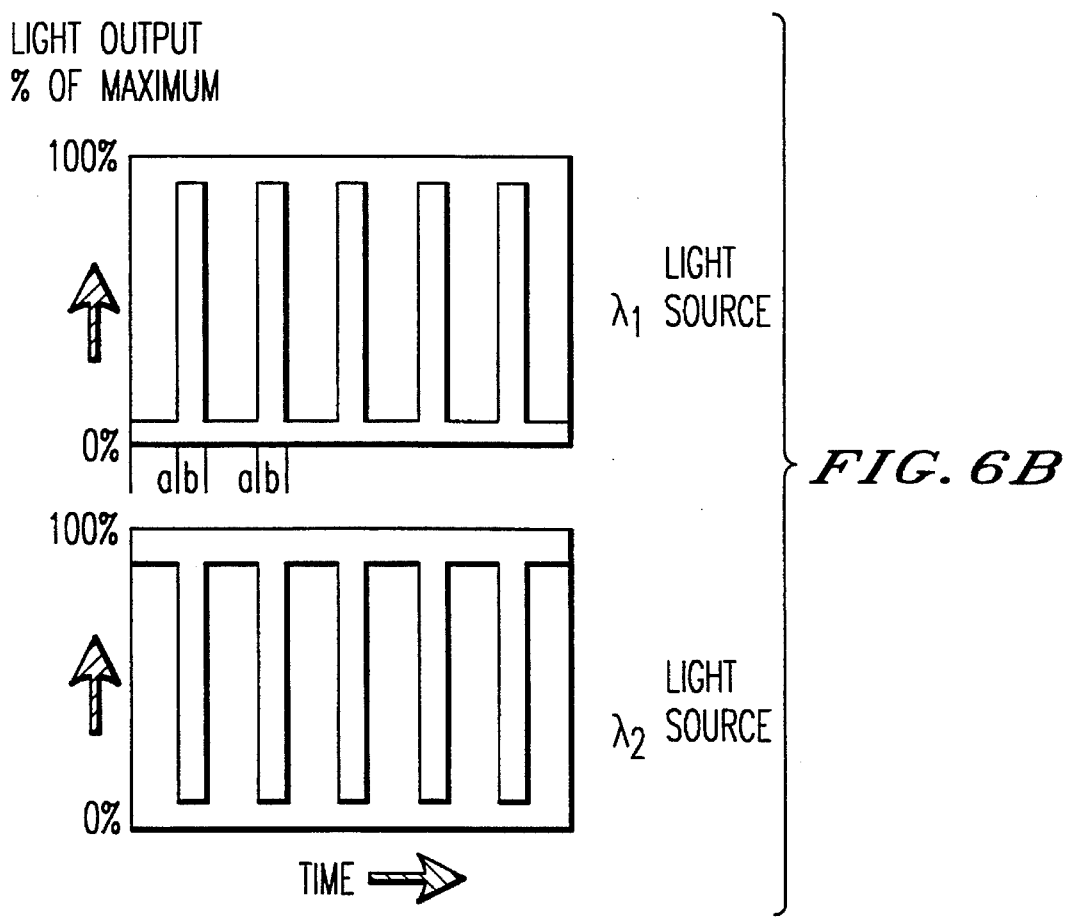

As shown in FIG. 5, if the relatively high and low proportions of current are alternated between the first light source 52 and the second light source 53, and the intensities of each light beam generated is monitored with first and second detectors 56 and 57, the time-versus-light intensities shown in FIGS. 6A and 6B are observed. First and second detectors 56 and 57 are, for example, high speed photodiode detectors. The instantaneous application of increased current leads to an immediate increase in light intensity. Likewise, an immediate reduction of current leads to an immediate and proportional loss of light output (intensity). In the example shown in FIGS. 6A and 6B, the length of time for a single irradiation with $\lambda_1$ or $\lambda_2$ can be varied from as short as 1 nanosecond to a length theoretically approaching infinity, but for practical reasons, may be as long as 2–4 hours, with the resultant repeatability shown in FIGS. 6A and 6B.

Referring to FIGS. 6A and 6B, the period of time "a" which the sample is irradiated with $\lambda_2$ light and/or the period time "b" which the sample is irradiated $\lambda_1$ light can be for any duration which can be controlled electronically. In theory, there is no upper limit to the length of time which the sample can be irradiated with either or both wavelengths of light. However, from a practical perspective, the sample is irradiated with a single wavelength of light for a length of time of from 1 ns to 24 h, but more advantageously, from 1 ns to 1 s, and even more advantageously from 1 ns to 2.5 ms.

Figure 7:
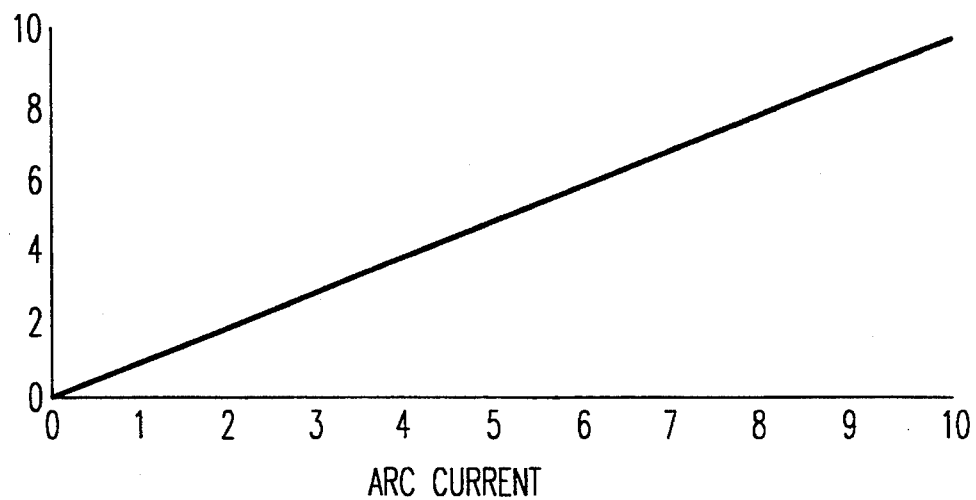
FIG. 7 illustrates the general relationship between arc current and light intensity.

Further, as shown by the graph in FIG. 7, the intensity of light output from either light source (e.g., arc lamp) is linearly proportional to the amount of current applied to the light source.

As shown in FIG. 8, the present invention can also be configured for fluorescent ratio photometry and imaging in a microscope by placing the components of the apparatus such that the two light sources 82 and 83 (e.g., arc lamp beams) are combined in a conventional beam combiner 84 to illuminate the specimen. For example, a suitable beam combiner is one manufactured by Carl Zeiss, Oberkochen, Germany. The electronic current control 81 alternates the illumination between the $\lambda_1$ light source 82 and the $\lambda_2$ light source 83 at a frequency of from 1 ns to 24 h per cycle, as desired.

An optional embodiment of the present illumination source employs a multiple arc lamp with pilot arc and running arc, preferably electrically connected to one another. Thus, an alternative method of arc intensity switching and an alternative apparatus in accordance with the present invention employs at least one light source in which two or more arcs are maintained (a multiple arc lamp), in which one arc is a pilot arc and another arc is a running arc.

In the present multiple arc lamp, one arc in each light source remains out of the optical axis in a "pilot" state, to maintain a minimum electric current in the light source, and another arc in each light source is positioned in the optical axis (the "running" arc). The running arc can be switched on or off, or have its intensity adjusted by electronically varying the current passing through it.

An embodiment of a multiple arc lamp with pilot arc and running arc is shown in FIG. 9. The main arc 91 (the "running" arc) is aligned with the optical axis 93 of the beam of light generated by the multiple arc lamp. A relatively high, pre-selected or desired amount of current is supplied by electronic current control means (not shown), and is passed through main arc 91 to provide a first wavelength of light $\lambda_1$ for irradiation of the sample. The electronic current control means provides a minimum current to pilot arc 92 to maintain the "pilot" state.

When the pilot arc is electrically connected to the running arc, the function of the pilot arc is to maintain a minimum electric current through the light-providing means (the multiple arcs) of the light source. This embodiment is particularly advantageous for a method in which the running arc is alternately switched on and off. When the electric current passing through the running arc is increased to a relatively high value (from a relatively low value or from zero current), the pilot arc provides a current which instantaneously re-establishes the arc in the running arc. A further advantage of the present multiple arc lamp is that the light generated by the pilot arc is not aligned (substantially or completely out of alignment) with the optical axis. Thus, the multiple arc lamp generates less interference light from an arc maintained in a "pilot" state than a single-arc lamp.

To switch the wavelength of sample irradiation light from $\lambda_1$ to $\lambda_2$, the electronic current control means decreases the current in the main arc 91 to a minimum current, or preferably, to zero current. Either simultaneously or sequentially, the current to a second light source (which is not shown in FIG. 9, and which may be either a single- or multiple-arc lamp) is increased sufficiently to provide excitation wavelength $\lambda_2$ for irradiation of the sample. The current provided to pilot arc 92 is kept at a minimum current (as defined above), and advantageously is kept at a constant current. In a particularly advantageous embodiment, the second light source is a second multiple-arc lamp, and switching the wavelength or intensity of sample irradiation light comprises increasing the current to the running arc of the second light multiple-arc lamp sufficiently to provide a light beam of wavelength $\lambda_2$ or having a second intensity.

The present illumination source and apparatus are particularly useful in methods of emission ratio photometry and emission ratio imaging, including multiple emission ratio photometry and imaging, and fluorescent emission ratio photometry and imaging. However, the present invention is not limited to these specific utilities.

Thus, a further aspect of the present invention concerns an apparatus for luminescence emission photometry, comprising:

(a) a first light source which generates a first light beam having sufficient energy to electronically excite at least one luminescent compound in a sample, (b) a second light source which generates a second light beam having sufficient energy to electronically excite at least one luminescent compound in said sample, (c) a controlling means for controlling electric current to each of the first and second light sources, the controlling means being electrically connected to each of the first and second light sources, (d) a first means for selecting a wavelength of light, positioned in the path of the first light beam to provide the first light beam with a first wavelength, (e) a second means for selecting a wavelength of light, positioned in the path of the second light beam to provide the second light beam with a second wavelength, the second wavelength differing from the first wavelength, (f) a mounting platform for said sample, positioned such that each of the first and second light beams strikes the sample so that the luminescent compound produces a luminescent emission, and (g) a detector positioned to receive the luminescent emission.

In preferred embodiments, the present apparatus for luminescence emission photometry may further comprise:

(h-1) a dichroic mirror positioned in the path of each of the first and second light beams (respectively having first and second wavelengths) to reflect each of the first and second light beams to a location on the mounting platform where the sample may be located;

(h-2) a beam combiner;

(h-3) a second detector;

or any combination thereof.

In a further aspect of the present apparatus for luminescence emission photometry, the detector (d) (and/or the second detector (h-3)) has an electronic switching device (e.g., 47 in FIG. 4) for adjusting the sensitivity of the detector at least two times within a period of time of from about 2 ns to 1 minute.

In a preferred embodiment, the detector comprises a camera having a photosensitive element and a means for augmenting the electrical signals produced in the photosensitive element, such as the detector described in U.S. application Ser. No. 07/935,873, filed on Aug. 26, 1992, now U.S. Pat. No. 5,332,905. A conventional intensified charge-couple device (CCD), known to those in the art, is suitable for use as the detector. However, a preferred camera which includes the preferred photosensitive element and a means for augmenting the electrical signals is that accompanying the ATTOFLUOR™ Digital Fluorescence Microscopy System (Trademark, Atto Instruments, Rockville, Md.).

In the embodiment comprising a second detector, the first detector (detector (g) above) detects an emission from the sample in response to excitation by the first light beam. The second detector detects an emission from the sample in response to excitation by the second light beam.

Optionally, the detector can be fitted with first and second cameras. A conventional beam-splitter may be used to separate the reflected emission beam into component wavelength ranges, prior to interception of the emission beam by filters made of one or more suitable, conventional wavelength-selective materials, which are generally known in the art. The emission beam wavelength range reflected to camera 7(a) by is beam-splitter 8 is directed towards filter 10(a) by a prism or mirror 11. The two-camera system provides an advantage in the precise simultaneous monitoring of two separate, independent emissions. However, the disadvantage of the two-camera system is that the photosensors must be exactly aligned to provide reliable results.

A further aspect of the present invention concerns a method of determining the concentration of a luminescence-affecting chemical species in a sample capable of emitting luminescent radiation, comprising the steps of:

(A) irradiating the sample with light having a first wavelength and having sufficient energy to cause the sample to emit a first luminescent emission; then, within a period of time of from 1 ns to 1 min, (B) irradiating the sample with light having a second wavelength and having sufficient energy to cause the sample to emit a second luminescent emission, (C) measuring the intensity of each of the first and second luminescent emissions, (D) determining a ratio of one of the luminescent emission intensities to the remaining one of the luminescent emission intensities, and (E) correlating the ratio to the concentration of the luminescence-affecting chemical species in the sample.

In a preferred embodiment of the present invention, the luminescence is fluorescence.

Other features of the invention will become apparent in the course of the following descriptions of exemplary embodiments which are given for illustration of the invention and are not intended to be limiting thereof.

EXAMPLE 1

Cultured astrocytoma cells grown on glass coverslips are labeled with 5 µM Fura-2 AM (a fluorescent dye, commercially available from Molecular Probes, Junction City, Oreg.) for 20 minutes in physiological salt solution containing 5 mM glucose. The cells are washed to remove the excess Fura-2 AM from the media. The cells are then mounted on the stage of a Zeiss Axiovert 135 microscope, and are observed with a Zeiss Achrostigmat 40 power oil immersion objective. The cells were excited (irradiated) with a dual-excitation light source (containing first and second arcs or light sources). The respective current for each light source is controlled by a computer, represented by controlling means 51 shown in the schematic diagram in FIG. 5. The beams are combined using a beam combiner 84 (manufactured by Carl Zeiss, Oberkochen, Germany), as shown in FIG. 8. With reference to FIG. 5, first and second arc sources 52 and 53 are each 100 watt mercury arc sources, interference filter 54 is a 10 nm bandpass (band width) filter which passes light having an average wavelength of 334 nm, and interference filter 55 is a 10 nm bandpass filter which passes light having an average wavelength of 380 nm. A dichroic mirror, which separates the excitation light from the emission light by reflecting light below 395 nm and passing light above this wavelength, is positioned to intercept both first and second light beams generated by the dual-excitation light source as well as emissions from the sample. For example, referring to FIG. 4, the excitation beam generated by light source 41 (with alternating 334 nm and 380 nm light) strikes the dichroic mirror 43 and is reflected up to the cell sample 44. Fluorescence emissions from cells loaded with Fura-2 (and/or Fura-2 AM) are in the range of 500 nm light. The fluorescence emissions pass through the dichroic mirror 43 and are reflected up to the camera or photodetector 46 after passing through a 495 nm long-pass filter, positioned in the light path between the dichroic mirror and the photodetector. Alternating the illumination between 334 and 380 nm causes the cells to alternately emit fluorescence proportionally to the concentration of calcium ion in the cells.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A vibration-free method of irradiating a sample, comprising the steps of:

(A) irradiating said sample with light having a first wavelength, a first intensity or both a first wavelength and a first intensity, by passing an electric current having a first value through a first arc and passing an electric current having a second value through a second arc, said first value being greater than said second value; and within a period of time of from 1 nanosecond (1 ns) to 1 second (1 s) of said irradiating step (A), (B) irradiating said sample with light having a second wavelength, a second intensity or both a second wavelength and a second intensity by reducing the value of said electric current passed through said first light source to a third value and increasing said electric current through said second light source to a fourth value, said fourth value being greater than said third value, wherein each of said arcs has a wattage of from 10 to 2000 W.

2. The method of claim 1, further comprising, within a period of time of from 1 ns to 1 s after said irradiating step (B), repeating said irradiating step (A).

3. The method of claim 1, wherein said first current is greater than 90% of the total of said first and second currents.

4. The method of claim 1, wherein said irradiating step (A) irradiates said sample with light having a first wavelength and a first intensity, and said irradiating step (B) irradiates said sample with light having a second wavelength and a second intensity, wherein said second wavelength differs from said first wavelength.

5. The method of claim 1, wherein said irradiating step (B) is conducted within a period of time of from 1 ns to 2.5 milliseconds.

6. An apparatus for sequentially irradiating a sample with two or more wavelengths, intensities, or wavelengths and intensities of light, comprising:

(A) a first arc which generates a first light beam having a first wavelength, a first intensity or both a first wavelength and a first intensity;

(B) a second arc which generates a second light beam having a second wavelength, a second intensity or both a second wavelength and a second intensity, wherein said second wavelength differs from said first wavelength, said second intensity differs from said first intensity, or said second wavelength and said second intensity differ from said first wavelength and said first intensity; and (C) a controlling means for controlling electric current to each of said first and second arcs, said controlling means being electrically connected to each of said first and second arcs, wherein each of said first and second arcs has a wattage of from 10 to 2000 W.

7. The apparatus of claim 6, further comprising:

(D) a first vibration-free means for selecting a band of light which intercepts said first light beam, and (E) a second vibration-free means for selecting a band of light which intercepts said second light beam.

8. The apparatus of claim 7, wherein said apparatus sequentially irradiates a sample with two or more wavelengths of light, said first wavelength is a mean or average wavelength of a first band of wavelengths, and said second wavelength is a mean or average wavelength of a second band of wavelengths, each of said first and second bands of wavelengths either (a) having a band width of 40 nm or less, or (b) being greater than or equal to a desired or pre-selected wavelength.

9. The apparatus of claim 6, further comprising a beam combiner.

10. The apparatus of claim 6, further comprising at least one additional light source.

11. The apparatus of claim 6, wherein said controlling means provides a minimum current to one of said first and second arcs and a larger current to the other of said first and second arcs, wherein said minimum current is one sufficient to support a small arc, but one which does not cause interference with measurement of an emission resulting from irradiating said sample with light from said other of said first and second arcs.

12. The apparatus of claim 6, wherein at least one of said first and second light sources is a multiple arc lamp, comprising a pilot arc and a running arc.

13. The apparatus of claim 12, wherein said pilot arc and said running arc are electrically connected to one another.

14. The apparatus of claim 12, wherein the beam of light generated by said multiple arc lamp has an optical axis, said running arc is aligned with said optical axis, and said pilot arc is not aligned with said optical axis.

15. An apparatus for luminescence emission photometry, comprising:

(a) a first arc which generates a first light beam having sufficient energy to electronically excite at least one luminescent compound in a sample, (b) a second arc which generates a second light beam having sufficient energy to electronically excite at least one luminescent compound in said sample, (c) a controlling means for controlling electric current to each of said first and second arcs, said controlling means being electrically connected to each of said first and second arcs, (d) a first vibration-free means for selecting a wavelength of light, positioned in the path of said first light beam to provide said first light beam with a first wavelength, (e) a second vibration-free means for selecting a wavelength of light, positioned in the path of said second light beam to provide said second light beam with a second wavelength, said second wavelength differing from said first wavelength, (f) a mounting platform for said sample, positioned such that each of said first and second light beams strikes said sample so that said luminescent compound produces a luminescent emission, and (g) a detector positioned to receive said luminescent emission, wherein each of said first and second arcs has a wattage of from 10 to 2000 W.

16. The apparatus of claim 15, further comprising:

(h) a dichroic mirror positioned in the path of each of said first and second light beams, to reflect each of said first and second light beams to a location on said mounting platform where said sample may be located.

17. The apparatus of claim 15, wherein said detector has an electronic switching device for adjusting the sensitivity of said detector at least two times within a period of time of from about 2 ns to 1 min.

18. The apparatus of claim 15, further comprising a beam combiner.

19. The apparatus of claim 15, wherein said detector detects an emission from said sample in response to excitation by said first light beam, and said apparatus further comprises a second detector which detects an emission from said sample in response to excitation by said second light beam.

20. A vibration-free method of determining the concentration of a luminescence-affecting chemical species in a sample capable of emitting luminescent radiation, comprising the steps of:

(A) irradiating said sample with light having a first wavelength and having sufficient energy to cause said sample to emit a first luminescent emission by passing an electric current having a first value through a first arc and passing an electric current having a second value through a second arc, said first value being greater than said second value;

then, within a period of time of from 1 ns to 1 s, (B) irradiating said sample with light having a second wavelength and having sufficient energy to cause said sample to emit a second luminescent emission by reducing the value of said electric current passed through said first light source to a third value and increasing said electric current through said second light source to a fourth value, said fourth value being greater than said third value, (C) measuring the intensity of each of said first and second luminescent emissions, (D) determining a ratio of one of said first and second luminescent emission intensities to the remaining one of said first and second luminescent emission intensities, and (E) correlating said ratio to said concentration of said luminescence-affecting chemical species in said sample, wherein each of said arcs has a wattage of from 10 to 2000 W.

21. The method of claim 20, wherein said luminescence is fluorescence.

* * * * *